US008673845B2

(12) United States Patent
Kobayashi et al.

(10) Patent No.: US 8,673,845 B2
(45) Date of Patent: *Mar. 18, 2014

(54) CARRIER PEPTIDE FRAGMENT AND USE THEREOF

(75) Inventors: Nahoko Kobayashi, Tsukuba (JP); Tetsuhiko Yoshida, Tsukuba (JP); Mikio Niwa, Tsukuba (JP); Kenichi Tanaka, Tsukuba (JP)

(73) Assignee: Toagosei Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/386,582

(22) PCT Filed: Jul. 28, 2010

(86) PCT No.: PCT/JP2010/062691
§ 371 (c)(1),
(2), (4) Date: Jan. 23, 2012

(87) PCT Pub. No.: WO2011/013698
PCT Pub. Date: Feb. 3, 2011

(65) Prior Publication Data
US 2012/0122225 A1    May 17, 2012

(30) Foreign Application Priority Data
Jul. 29, 2009    (JP) .................................. 2009-177101

(51) Int. Cl.
*A61K 38/02*    (2006.01)
*A61K 38/18*    (2006.01)
*C12N 5/02*    (2006.01)

(52) U.S. Cl.
USPC ........................... 514/1.2; 514/21.2; 530/300

(58) Field of Classification Search
None
See application file for complete search history.

(56) References Cited

U.S. PATENT DOCUMENTS

| | | | |
|---|---|---|---|
| 4,867,975 A * | 9/1989 | Gelb, Jr. .................... | 424/222.1 |
| 6,037,521 A | 3/2000 | Sato et al. | |
| 6,340,583 B1 | 1/2002 | Yan et al. | |
| 6,403,353 B1 | 6/2002 | Yan et al. | |
| 6,423,684 B1 | 7/2002 | Mochly-Rosen et al. | |
| 2003/0125242 A1 | 7/2003 | Rosenecker et al. | |
| 2003/0166215 A1 | 9/2003 | Yan et al. | |
| 2003/0229202 A1 | 12/2003 | Guo et al. | |
| 2004/0175751 A1 | 9/2004 | Yan et al. | |
| 2004/0186052 A1 | 9/2004 | Iyer et al. | |
| 2004/0226056 A1 | 11/2004 | Roch et al. | |
| 2006/0100134 A1 | 5/2006 | Guo et al. | |
| 2006/0166917 A1 | 7/2006 | Lindeman et al. | |
| 2006/0270834 A1 | 11/2006 | Kanno | |
| 2007/0065941 A1 | 3/2007 | Kondo et al. | |
| 2008/0076145 A1 | 3/2008 | Cummings et al. | |
| 2009/0253618 A1 | 10/2009 | Kanno et al. | |
| 2010/0297758 A1 | 11/2010 | Yoshida et al. | |
| 2012/0035112 A1 | 2/2012 | Yoshida et al. | |
| 2012/0122210 A1 | 5/2012 | Yoshida et al. | |
| 2012/0208752 A1 | 8/2012 | Yoshida et al. | |
| 2013/0005034 A1 | 1/2013 | Yoshida et al. | |
| 2013/0079273 A1 | 3/2013 | Yoshida et al. | |

FOREIGN PATENT DOCUMENTS

| | | |
|---|---|---|
| EP | 1 918 297 A1 | 5/2008 |
| JP | A-7-132033 | 5/1995 |
| JP | A-9-323928 | 12/1997 |
| JP | A-2001-199997 | 7/2001 |
| JP | A-2003-137899 | 5/2003 |
| JP | A-2004-357543 | 12/2004 |
| JP | A-2005-154338 | 6/2005 |
| JP | A-2005-330206 | 12/2005 |
| JP | B2-3854995 | 12/2006 |
| JP | A-2007-145761 | 6/2007 |
| JP | A-2007-159429 | 6/2007 |
| JP | A-2009-209064 | 9/2009 |
| JP | A-2011-016763 | 1/2011 |
| WO | WO 02/18572 A2 | 3/2002 |
| WO | WO 02/077171 A2 | 10/2002 |
| WO | WO 03/076561 A2 | 9/2003 |
| WO | WO 2004/056854 A1 | 7/2004 |
| WO | WO 2005/086800 A2 | 9/2005 |
| WO | WO 2007/010989 A1 | 1/2007 |
| WO | WO 2007/149293 A2 | 12/2007 |
| WO | WO 2008/008569 A2 | 1/2008 |

(Continued)

OTHER PUBLICATIONS

Bochkov et al, Phylogenetic analysis of partial S1 and N gene sequences of infectious bronchitis virus isolates from Italy revealed genetic diversity and recombination, Virus Genes, 2007, 35, pp. 65-71.*

(Continued)

*Primary Examiner* — Julie Ha
*Assistant Examiner* — Li Ni Komatsu
(74) *Attorney, Agent, or Firm* — Oliff PLC

(57) ABSTRACT

The method for transferring a foreign substance provided by the present invention includes the steps of: preparing a construct for transferring a foreign substance that contains a carrier peptide fragment including either the amino acid sequence WRRQARFK (SEQ ID NO. 1) or any amino acid sequence formed by the substitution, deletion, and/or addition (insertion) of 1, 2, or 3 amino acid residues in the amino acid sequence, and a foreign substance of interest that is bonded to the N-terminus and/or C-terminus of the carrier peptide fragment; supplying the construct for transferring a foreign substance to a test sample that contains a target eukaryotic cell; and incubating the test sample that has been supplied with the construct for transferring a foreign substance to thereby transfer the construct into the eukaryotic cell in the test sample.

4 Claims, 4 Drawing Sheets

(56) References Cited

FOREIGN PATENT DOCUMENTS

| WO | WO 2009/093692 A1 | 7/2009 |
|---|---|---|
| WO | WO 2010/117078 A1 | 10/2010 |
| WO | WO 2010/117079 A1 | 10/2010 |

OTHER PUBLICATIONS

NCBI database Accession No. Q1M2X0, p. 1, accessed Nov. 7, 2012.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Egies et al, Establishment of human embryonic stem cell-transfected clones carrying a marker for undifferentiated cells, Current Biology, 2001, 11, pp. 514-518.*
Dieterlen-Lievre, On the origin of haemopoietic stem cells in the avian embryo: an experimental approach, J. Embryol. Exp. Morph., 1975, 33, pp. 607-619.*
Emmott et al., "Nucleolar targeting: the hub of the matter," *European Molecular Biology Organization*, vol. 10, No. 3, 2009, pp. 231-238.
Reed et al., "Delineation and Modelling of a Nucleolar Retention Signal in the Coronavirus Nucleocapsid Protein," *Traffic*, vol. 7, 2006, pp. 833-848.
Hilton et al., "Twenty proteins containg a C-terminal SOCS box form five structural classes," *Proc. Natl. Acad. Sci. USA*, vol. 95, 1998, pp. 114-119.
Kamura et al., "The Elongin BC complex interacts with the conserved SOCS-box motif present in members of the SOCS, ras, WD-40 repeat, and ankyrin repeat families," *Genes & Development*, vol. 12, 1998, pp. 3872-3881.
Yu et al., "Selective assembly of HIV-1 Vif-Cul5-ElonginB-ElonginC E3 ubiquitin ligase complex through a novel SOCS box and upstream cysteines," *Genes & Development*, vol. 18, 2004, pp. 2867-2872.
Kamura et al., "VHL-box and SOCS-box domains determine binding specificity for Cul2-Rbx1 and Cul5-Rbx2 modules of ubiquitin ligases," *Genes & Development*, vol. 18, 2004, pp. 3055-3065.
Boursnell et al., "Sequences of the Nucleocapsid Genes from Two Strains of Avian Infectious Bronchitis Virus," *J. gen. Virol.*, vol. 66, 1985, pp. 573-580.
Fang et al., "Selection of and recombination between minor variants lead to the adaptation of an avian coronavirus to primate cells," *Biochemical and Biophysical Research Communications*, vol. 336, 2005, pp. 417-423.
Oct. 5, 2010 International Search Report issued in International Patent Application No. PCT/JP2010/062693 (with translation).
Cserpán et al., "The Mechanism of Nuclear Transport of Natural or Artificial Transport Substrates in Digitonin-Permeabilized Cells," Journal of Cell Science, vol. 108, pp. 1849-1861, 1995.
Futaki et al., "Intracellular Protein Delivery Using Membrane-Permeable Peptides," Seibutsu to Kagaku, vol. 43, No. 10, pp. 649-653, 2005, with English-language translation.
Goyal et al., "Phosphorylation-Dependent Regulation of Unique Nuclear and Nucleolar Localization Signals of LIM Kinase 2 in Endothelial Cells," Journal of Biological Chemistry, vol. 281, No. 35, pp. 25223-25230, Sep. 1, 2006.
Kang et al., "The Precursor of Alzheimer's Disease Amyloid A4 Protein Resembles a Cell-Surface Receptor," Nature, vol. 325, pp. 733-736, Feb. 19, 1987.
Kile et al., "The Suppressors of Cytokine Signalling (SOCS)," Cellular and Molecular Life Sciences, vol. 58 , pp. 1627-1635, 2001.
Kobayashi et al., "Nucleolar Localization Signals of LIM Kinase 2 Function as a Cell-Penetrating Peptide," Protein & Peptide Letters, vol. 17, pp. 1480-1488, 2010.
Kwak et al., "Amyloid Precursor Protein Regulates Differentiation of Human Neural Stem Cells," Stem Cells Dev., vol. 15, No. 3, pp. 381-389, 2006.
Liu et al., "Rack1 Competes with HSP90 for Binding to HIF-1α and is Required for $O_2$-Independent and HSP90 Inhibitor-Induced Degradation of HIF-1α," Molecular Cell, vol. 25, pp. 207-217, Jan. 26, 2007.
Liu et al., "Calcineurin Promotes Hypoxia-Inducible Factor 1α Expression by Dephosphorylating RACK1 and Blocking Rack1 Dimerization," Journal of Biological Chemistry, vol. 282, No. 51, pp. 37064-37073, Dec. 21, 2007.
Liu et al., "Rack1 vs. HSP90: Competition for HIF-1α Degradation vs. Stablization," Cell Cycle, vol. 6, No. 6, pp. 656-659, Mar. 15, 2007.
Martoglio et al., "Signal Sequences: More than just Greasy Peptides," Trends in Cell Biology, vol. 8, pp. 410-415, Oct. 1998.
Marutle et al., "Modulation of Human Neural Stem Cell Differentiation in Alzheimer (APP23) Transgenic Mice by Phenserine," Proc. Natl. Acad. USA, vol. 104, No. 30, pp. 12506-12511, Jul. 24, 2007.
Pokorska et al., "The Analysis of the Transcriptional Activator PrnA Reveals a Tripartite Nuclear Localisation Sequence," J. Mil. Biol., vol. 298, pp. 585-596, 2000.
Sugaya et al., "Practical Issues in Stem Cell Therapy for Alzheimer's Disease," Curr. Alzheimer Res., vol. 4, No. 4, pp. 370-377, 2007 (Abstract Only).
Takei et al., "Possible Involvement of a Pertussis Toxin-Sensitive GTP-Binding Protein in Protein Transport into Nuclei Isolated from Rat Liver," J. Biochem., vol. 115, pp. 578-583, 1994.
Mar. 1, 2011 European Search Report issued in European Application No. 09 704 366.5.
Dec. 5, 2011 European Office Action issued in European Application No. 09 704 366.5.
Apr. 7, 2009 International Search Report issued in International Application No. PCT/2009/051082.
Jul. 13, 2010 International Search Report issued in International Application No. PCT/JP2010/056510 (with translation).
Oct. 5, 2010 International Search Report issued in International Patent Application No. PCT/JP2010/062693 (with translation).
Jan. 18, 2011 International Search Report issued in International Patent Application No. PCT/JP2010/069165.
Jul. 19, 2011 International Search Report issued in International Application No. PCT/JP2011/062809.
Jun. 12, 2012 International Preliminary Report on Patentability and Written Opinion issued in International Patent Application No. PCT/JP2010/069165.
Jan. 8, 2013 International Preliminary Report on Patentability and Written Opinion issued in International Application No. PCT/JP2011/062809.
Mar. 29, 2010 International Preliminary Report on Patentability and Written Opinion issued in International Application No. PCT/JP2009/051082.
Aug. 17, 2011 Office Action issued in U.S. Appl. No. 12/864,147.
Sep. 30, 2011 Office Action issued in U.S. Appl. No. 12/864,147.
Mar. 12, 2012 Office Action issued in U.S. Appl. No. 12/864,147.
Nov. 14, 2012 Office Action issued in U.S. Appl. No. 13/386,539.
Jan. 31, 2013 Office Action issued in U.S. Appl. No. 13/258,788.
Feb. 22, 2013 Office Action issued in U.S. Appl. No. 13/386,539.
Apr. 17, 2013 Office Action issued in U.S. Appl. No. 13/503,220.
Alexander et al., "The Role of Suppressors of Cytokine Signaling (SOCS) Proteins in Regulation of the Immune Response," Annu. Rev. Immunol., vol. 22, pp. 503-529, 2004.
Larsen et al., "Suppressors of Cytokine Signalling: SOCS," APMIS, vol. 110, pp. 833-844, 2002.
Jun. 18, 2013 Supplementary European Search Report issued in European Application No. 10 82 6811.
Aug. 7, 2013 Office Action issued in U.S. Appl. No. 13/258,788.
Selkoe, "Normal and Abnormal Biology of the Beta-Amyloid Precursor Protein," Annu. Rev. Neurosci., vol. 17, pp. 489-517, 1994.

(56) References Cited

OTHER PUBLICATIONS

Hayashi et al., "Alzheimer Amyloid Protein Precursor Enhances Proliferation of Neural Stem Cells from Fetal Rat Brain," Biochemical and Biophysical Research Communications, vol. 205, No. 1, pp. 936-943, 1994.

Venkataramani et al., "Histone Deacetylase Inhibitor Valproic Acid Inhibits Cancer Cell Proliferation via Down-Regulation of the Alzheimer Amyloid Precursor Protein," The Journal of Biological Chemistry, vol. 285, No. 14, pp. 10678-10689, Apr. 2, 2010.

Kwak, "Studies on the Novel Function of Amyloid Precursor Protein in Glial Differentiation of Neural Stem Cells," Dissertation, pp. 1-173, 2006.

Oct. 16, 2013 Office Action issued in U.S. Appl. No. 13/701,747.

* cited by examiner

SEQUENCE LISTING

<160> NUMBER OF SEQ ID NOS: 82

<210> SEQ ID NO 1

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Trp Arg Arg Gln Ala Arg Phe Lys
1               5

<210> SEQ ID NO 2
<211> LENGTH: 15
<212> TYPE: PRT
<213> ORGANISM: Artificial sequence
<220> FEATURE:
<223> OTHER INFORMATION: Synthetic peptide

<400> SEQUENCE: 2

Pro Leu Gln Glu Leu Cys Arg Gln Arg Ile Val Ala Ala Val Gly
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Synthetic peptide

<400> SEQUENCE: 3

Thr Leu Gln His Phe Cys Arg Leu Ala Ile Asn Lys Cys Thr Gly
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Synthetic peptide

<400> SEQUENCE: 4

Thr Leu Gln His Leu Cys Arg Lys Thr Val Asn Gly His Leu Asp
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: Synthetic peptide

<400> SEQUENCE: 5

Ser Leu Gln His Ile Cys Arg Thr Val Ile Cys Asn Cys Thr Thr
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: Synthetic peptide

<400> SEQUENCE: 6

Ser Leu Gln Tyr Ile Cys Arg Ala Val Ile Cys Arg Cys Thr Thr
1               5                   10                  15

<210> SEQ ID NO 7
<211> LENGTH: 15
<212> TYPE: PRT
```

```
<213> ORGANISM: Artificial sequence
<220> FEATURE:
<223> OTHER INFORMATION: Synthetic peptide

<400> SEQUENCE: 7

Ser Leu Gln Tyr Leu Cys Arg Phe Val Ile Arg Gln Tyr Thr Arg
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: Synthetic peptide

<400> SEQUENCE: 8

Ser Leu Gln His Leu Cys Arg Phe Arg Ile Arg Gln Leu Val Arg
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic peptide

<400> SEQUENCE: 9

Ser Leu Gln Asp Leu Cys Cys Arg Ala Val Val Ser Cys Thr Pro
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Ser Leu Gln Asp Leu Cys Cys Arg Thr Ile Val Ser Cys Thr Pro
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic peptide

<400> SEQUENCE: 11

Ser Leu Gln His Ile Cys Arg Met Ser Ile Arg Arg Val Met Ser
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic peptide

<400> SEQUENCE: 12

Ser Leu Lys His Leu Cys Arg Lys Ala Leu Arg Ser Phe Leu Thr
1               5                   10                  15

<210> SEQ ID NO 13
<211> LENGTH: 15
<212> TYPE: PRT
<213> ORGANISM: Artificial sequence
<220> FEATURE:
```

<223> OTHER INFORMATION: Synthetic peptide

<400> SEQUENCE: 13

Thr Leu Leu Ser Leu Cys Arg Val Ala Val Arg Arg Ala Leu Gly
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Synthetic peptide

<400> SEQUENCE: 14

Pro Leu Ala His Leu Cys Arg Leu Arg Val Arg Lys Ala Ile Gly
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Synthetic peptide

<400> SEQUENCE: 15

Ser Leu Thr His Leu Cys Arg Leu Glu Ile Arg Ser Ser Ile Lys
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Synthetic peptide

<400> SEQUENCE: 16

Thr Leu Leu Glu Ser Ser Ala Arg Thr Ile Leu His Asn Arg Ile
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Synthetic peptide

<400> SEQUENCE: 17

Asn Leu Gln Asp Leu Cys Arg Ile Lys Ile Arg Gln Cys Ile Gly
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: Synthetic peptide

<400> SEQUENCE: 18

Ser Leu Gln His Leu Cys Arg Cys Ala Leu Arg Ser His Leu Glu
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 19

Ser Leu Lys His Leu Cys Arg Leu Lys Ile Arg Lys Cys Met Gly
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Synthetic peptide

<400> SEQUENCE: 20

Pro Leu Gln Glu Leu Cys Arg Gln Arg Ile Val Ala Thr Val Gly
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Synthetic peptide

<400> SEQUENCE: 21

Pro Leu Ala His Leu Cys Arg Leu Arg Val Arg Lys Ala Ile Gly
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Synthetic peptide

<400> SEQUENCE: 22

Ser Leu Gln His Leu Cys Arg Met Ser Ile Arg Arg Val Met Pro
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Synthetic peptide

<400> SEQUENCE: 23

Ser Leu Gln Asp Leu Cys Cys Arg Ala Val Val Ser Cys Thr Pro
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: Synthetic peptide

<400> SEQUENCE: 24

Ser Leu Gln Tyr Leu Ala Leu Thr Ala Leu Ile Thr Pro Lys Lys
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: Synthetic peptide

<400> SEQUENCE: 25
```

```
Ser Leu Gln Phe Leu Ala Leu Thr Val Tyr Thr Asp Phe Leu Arg
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic peptide

<400> SEQUENCE: 26

Ser Leu Gln Tyr Leu Ala Leu Arg Val Tyr Thr Asn Gly Leu Arg
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Synthetic peptide

<400> SEQUENCE: 27

Ser Leu Gln Leu Leu Ala Leu Val Ala Tyr Thr Asn Gly Ile Arg
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: Synthetic peptide

<400> SEQUENCE: 28

Ser Leu Gln Tyr Leu Ala Leu Leu Ala His Gln Asn Gly Leu Arg
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: Synthetic peptide

<400> SEQUENCE: 29

Ser Leu Gln Tyr Leu Ala Leu Gln Val Tyr Leu Lys Asp Gly Gly
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: Synthetic peptide

<400> SEQUENCE: 30

Ser Leu Gln Tyr Leu Ala Ile Lys Ala Trp Ala Arg Gln Gln Leu
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Synthetic peptide

<400> SEQUENCE: 31

Ser Leu Gln Tyr Leu Ala Leu Lys Val Val Ser Asp Val Arg Ser
1               5                   10                  15
```

<210> SEQ ID NO 32
<211> LENGTH: 15
<212> TYPE: PRT
<213> ORGANISM: Artificial sequence
<220> FEATURE:
<223> OTHER INFORMATION: Synthetic peptide

<400> SEQUENCE: 32

Ser Leu Gln Tyr Leu Ala Leu Thr Val Val Ser His Val Arg Ser
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: Synthetic peptide

<400> SEQUENCE: 33

Ser Leu Gln Phe Leu Ala Leu Val Val Val Gln Gln Asn Gly Arg
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: Synthetic peptide

<400> SEQUENCE: 34

Ser Leu Gln Phe Leu Ala Leu Arg Val Val Gln Glu Gly Lys Asn
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: Synthetic peptide

<400> SEQUENCE: 35

Ser Leu Gln Phe Leu Ala Leu Gln Val Val Gln Lys Gly His Gly
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: Synthetic peptide

<400> SEQUENCE: 36

Ser Leu Gln Phe Leu Cys Leu Arg Val Leu His Gly Gln Gln Glu
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic peptide

<400> SEQUENCE: 37

Ser Leu Gln Phe Leu Cys Leu Arg Gln Leu Gln His Val Gln Asn
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic peptide

<400> SEQUENCE: 38

Ser Leu Gln Phe Leu Cys Leu Arg Gln Leu Gln His Val Gln Ser
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: Synthetic peptide

<400> SEQUENCE: 39

Ser Leu Gln Tyr Leu Cys Leu Arg Gln Leu Gln His Val Gln Thr
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: Synthetic peptide

<400> SEQUENCE: 40

Ser Leu Gln Phe Ile Cys Leu Arg Gln Leu Gln His Val Gln Ala
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: Synthetic peptide

<400> SEQUENCE: 41

Ser Leu Gln Phe Leu Cys Leu Arg Val Ile Tyr Gly Pro Glu Glu
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: Synthetic peptide

<400> SEQUENCE: 42

Thr Leu Gln Phe Leu Cys Leu Gln Ala Tyr Leu Arg Gly Arg Lys
1               5                   10                  15

<210> SEQ ID NO 43
<211> LENGTH: 15
<212> TYPE: PRT
<213> ORGANISM: Artificial sequence
<220> FEATURE:
<223> OTHER INFORMATION: Synthetic peptide

<400> SEQUENCE: 43

Thr Leu Gln Leu Leu Cys Leu Arg Ala Tyr Ile Lys Phe Cys Arg
1               5                   10                  15

<210> SEQ ID NO 44
<211> LENGTH: 15

```
<212> TYPE: PRT
<213> ORGANISM: Artificial sequence
<220> FEATURE:
<223> OTHER INFORMATION: Synthetic peptide

<400> SEQUENCE: 44

Ser Leu Gln Cys Ile Ala Gly Gly Gln Val Leu Ala Ser Trp Phe
 1               5                  10                  15

<210> SEQ ID NO 45
<211> LENGTH: 15
<212> TYPE: PRT
<213> ORGANISM: Artificial sequence
<220> FEATURE:
<223> OTHER INFORMATION: Synthetic peptide

<400> SEQUENCE: 45

Ser Leu Gln Cys Met Ser Ala Gly Met Leu Leu Gly Arg Trp Phe
 1               5                  10                  15

<210> SEQ ID NO 46
<211> LENGTH: 15
<212> TYPE: PRT
<213> ORGANISM: Artificial sequence
<220> FEATURE:
<223> OTHER INFORMATION: Synthetic peptide

<400> SEQUENCE: 46

Ser Leu Gln Cys Met Ala Gly Gly Ala Val Leu Ala Val Trp Phe
 1               5                  10                  15

<210> SEQ ID NO 47
<211> LENGTH: 15
<212> TYPE: PRT
<213> ORGANISM: Artificial sequence
<220> FEATURE:
<223> OTHER INFORMATION: Synthetic peptide

<400> SEQUENCE: 47

Ser Leu Gln Cys Ile Ala Gly Gly Gln Val Leu Ala Ser Trp Phe
 1               5                  10                  15

<210> SEQ ID NO 48
<211> LENGTH: 15
<212> TYPE: PRT
<213> ORGANISM: Artificial sequence
<220> FEATURE:
<223> OTHER INFORMATION: Synthetic peptide

<400> SEQUENCE: 48

Ser Leu Gln Cys Arg Ala Gly Gly Thr Leu Leu Ala Val Trp Phe
 1               5                  10                  15

<210> SEQ ID NO 49
<211> LENGTH: 15
<212> TYPE: PRT
<213> ORGANISM: Artificial sequence
<220> FEATURE:
<223> OTHER INFORMATION: Synthetic peptide

<400> SEQUENCE: 49

Ser Leu Arg Cys Met Ala Gly Gly Ala Val Leu Ala Leu Trp Phe
 1               5                  10                  15

<210> SEQ ID NO 50
<211> LENGTH: 15
<212> TYPE: PRT
<213> ORGANISM: Artificial sequence
```

-continued

```
<220> FEATURE:
<223> OTHER INFORMATION: Synthetic peptide

<400> SEQUENCE: 50

Ser Leu Gln Cys Lys Ala Gly Gly Val Val Leu Ala Asn Trp Phe
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: Synthetic peptide

<400> SEQUENCE: 51

Ser Leu Arg Cys Met Ala Gly Gly Ala Val Leu Ala Leu Trp Phe
1               5                   10                  15

<210> SEQ ID NO 52
<211> LENGTH: 15
<212> TYPE: PRT
<213> ORGANISM: Artificial sequence
<220> FEATURE:
<223> OTHER INFORMATION: Synthetic peptide

<400> SEQUENCE: 52

Ser Leu Arg Cys Met Ala Gly Gly Ala Val Leu Ala Leu Trp Phe
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: Synthetic peptide

<400> SEQUENCE: 53

Ser Leu Arg Cys Met Ala Gly Gly Ala Val Leu Ala Leu Trp Phe
1               5                   10                  15

<210> SEQ ID NO 54
<211> LENGTH: 15
<212> TYPE: PRT
<213> ORGANISM: Artificial sequence
<220> FEATURE:
<223> OTHER INFORMATION: Synthetic peptide

<400> SEQUENCE: 54

Ser Leu Gln Cys Ile Ala Gly Gly Ala Val Leu Ala Ile Trp Phe
1               5                   10                  15

<210> SEQ ID NO 55
<211> LENGTH: 15
<212> TYPE: PRT
<213> ORGANISM: Artificial sequence
<220> FEATURE:
<223> OTHER INFORMATION: Synthetic peptide

<400> SEQUENCE: 55

Ser Leu Gln Cys Leu Ser Ala Thr Gln Val Leu Lys Glu Phe Leu
1               5                   10                  15

<210> SEQ ID NO 56
<211> LENGTH: 15
<212> TYPE: PRT
<213> ORGANISM: Artificial sequence
<220> FEATURE:
<223> OTHER INFORMATION: Synthetic peptide
```

```
<400> SEQUENCE: 56

Ser Leu Gln Cys Arg Ala Met Arg Arg Ile Leu Leu His Val Ile
1               5                   10                  15

<210> SEQ ID NO 57
<211> LENGTH: 15
<212> TYPE: PRT
<213> ORGANISM: Artificial sequence
<220> FEATURE:
<223> OTHER INFORMATION: Synthetic peptide

<400> SEQUENCE: 57

Ser Leu Gln Cys Leu Ala Ala Lys Gln Val Leu Leu Lys Cys Phe
1               5                   10                  15

<210> SEQ ID NO 58
<211> LENGTH: 15
<212> TYPE: PRT
<213> ORGANISM: Artificial sequence
<220> FEATURE:
<223> OTHER INFORMATION: Synthetic peptide

<400> SEQUENCE: 58

Ser Leu Gln Cys Leu Ala Ala Lys Ser Val Leu Leu Ser Cys Phe
1               5                   10                  15

<210> SEQ ID NO 59
<211> LENGTH: 17
<212> TYPE: PRT
<213> ORGANISM: Artificial sequence
<220> FEATURE:
<223> OTHER INFORMATION: Synthetic peptide

<400> SEQUENCE: 59

Ser Leu Gln Tyr Leu Ala Leu Lys Ala Leu Val Thr Pro Lys Lys Ile
1               5                   10                  15

Lys

<210> SEQ ID NO 60
<211> LENGTH: 17
<212> TYPE: PRT
<213> ORGANISM: Artificial sequence
<220> FEATURE:
<223> OTHER INFORMATION: Synthetic peptide

<400> SEQUENCE: 60

Ser Leu Gln Tyr Leu Ala Leu Ala Ala Leu Ile Thr Pro Lys Lys Ile
1               5                   10                  15

Lys

<210> SEQ ID NO 61
<211> LENGTH: 17
<212> TYPE: PRT
<213> ORGANISM: Artificial sequence
<220> FEATURE:
<223> OTHER INFORMATION: Synthetic peptide

<400> SEQUENCE: 61

Ser Leu Gln Tyr Leu Ala Leu Thr Ala Leu Ile Lys Pro Lys Lys Ile
1               5                   10                  15

Lys

<210> SEQ ID NO 62
<211> LENGTH: 17
```

```
<212> TYPE: PRT
<213> ORGANISM: Artificial sequence
<220> FEATURE:
<223> OTHER INFORMATION: Synthetic peptide

<400> SEQUENCE: 62

Ser Leu Gln Tyr Leu Ala Leu Thr Ala Leu Ile Thr Pro Lys Lys Ile
1               5                   10                  15
Lys

<210> SEQ ID NO 63
<211> LENGTH: 17
<212> TYPE: PRT
<213> ORGANISM: Artificial sequence
<220> FEATURE:
<223> OTHER INFORMATION: Synthetic peptide

<400> SEQUENCE: 63

Ser Leu Gln Tyr Leu Ala Leu Lys Ala Leu Val Thr Pro Thr Arg Thr
1               5                   10                  15
Arg

<210> SEQ ID NO 64
<211> LENGTH: 17
<212> TYPE: PRT
<213> ORGANISM: Artificial sequence
<220> FEATURE:
<223> OTHER INFORMATION: Synthetic peptide

<400> SEQUENCE: 64

Ser Leu Gln Tyr Leu Ala Leu Thr Ala Leu Val Ala Pro Lys Lys Thr
1               5                   10                  15
Lys

<210> SEQ ID NO 65
<211> LENGTH: 17
<212> TYPE: PRT
<213> ORGANISM: Artificial sequence
<220> FEATURE:
<223> OTHER INFORMATION: Synthetic peptide

<400> SEQUENCE: 65

Thr Leu Gln Leu Leu Ala Leu Arg Ala Val Val Lys Ala Arg Ser Arg
1               5                   10                  15
Lys

<210> SEQ ID NO 66
<211> LENGTH: 17
<212> TYPE: PRT
<213> ORGANISM: Artificial sequence
<220> FEATURE:
<223> OTHER INFORMATION: Synthetic peptide

<400> SEQUENCE: 66

Thr Leu Gln Phe Leu Ala Leu Lys Ala Val Val Lys Val Lys Arg Asn
1               5                   10                  15
Lys

<210> SEQ ID NO 67
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 67

Thr Leu Gln Tyr Leu Ala Leu Thr Ala Trp Val Gly Ala Lys Lys Arg
1               5                   10                  15

Lys

<210> SEQ ID NO 68
<211> LENGTH: 17
<212> TYPE: PRT
<213> ORGANISM: Artificial sequence
<220> FEATURE:
<223> OTHER INFORMATION: Synthetic peptide

<400> SEQUENCE: 68

Ser Leu Gln Phe Leu Ala Leu Lys Ala Leu Ile Ser Glu Arg Arg His
1               5                   10                  15

Arg

<210> SEQ ID NO 69
<211> LENGTH: 17
<212> TYPE: PRT
<213> ORGANISM: Artificial sequence
<220> FEATURE:
<223> OTHER INFORMATION: Synthetic peptide

<400> SEQUENCE: 69

Ser Leu Gln Phe Leu Ala Leu Lys Ala Leu Val Gly Gln Ser Lys Arg
1               5                   10                  15

Arg

<210> SEQ ID NO 70
<211> LENGTH: 17
<212> TYPE: PRT
<213> ORGANISM: Artificial sequence
<220> FEATURE:
<223> OTHER INFORMATION: Synthetic peptide

<400> SEQUENCE: 70

Ser Leu Gln Tyr Leu Ala Leu Arg Ala Trp Val Arg Val Gly Lys Lys
1               5                   10                  15

Lys

<210> SEQ ID NO 71
<211> LENGTH: 15
<212> TYPE: PRT
<213> ORGANISM: Artificial sequence
<220> FEATURE:
<223> OTHER INFORMATION: Synthetic peptide

<400> SEQUENCE: 71

Pro Leu Met Asp Leu Cys Arg Arg Ser Val Arg Leu Ala Leu Gly
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: Synthetic peptide

<400> SEQUENCE: 72

Ser Leu Leu His Leu Ser Arg Leu Cys Val Arg His Asn Leu Gly
1               5                   10                  15

<210> SEQ ID NO 73
```

```
<211> LENGTH: 15
<212> TYPE: PRT
<213> ORGANISM: Artificial sequence
<220> FEATURE:
<223> OTHER INFORMATION: Synthetic peptide

<400> SEQUENCE: 73

Pro Leu Met Asp Leu Cys Arg Arg Ser Ile Arg Ser Ala Leu Gly
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: Synthetic peptide

<400> SEQUENCE: 74

Ser Leu Gln Asp Leu Cys Cys Arg Ala Ile Val Ser Cys Thr Pro
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: Synthetic peptide

<400> SEQUENCE: 75

Ala Leu Phe Glu Leu Cys Gly Arg Ala Val Ser Ala His Met Gly
1               5                   10                  15

<210> SEQ ID NO 76
<211> LENGTH: 11
<212> TYPE: PRT
<213> ORGANISM: Artificial sequence
<220> FEATURE:
<223> OTHER INFORMATION: Synthetic peptide

<400> SEQUENCE: 76

Ser Leu Gln Cys Ile Ala Gly Gly Gln Val Leu
1               5                   10

<210> SEQ ID NO 77
<211> LENGTH: 11
<212> TYPE: PRT
<213> ORGANISM: Artificial sequence
<220> FEATURE:
<223> OTHER INFORMATION: Synthetic peptide

<400> SEQUENCE: 77

Ser Leu Gln His Leu Cys Arg Leu Val Ile Asn
1               5                   10

<210> SEQ ID NO 78
<211> LENGTH: 11
<212> TYPE: PRT
<213> ORGANISM: Artificial sequence
<220> FEATURE:
<223> OTHER INFORMATION: Synthetic peptide

<400> SEQUENCE: 78

Ser Leu Asn Lys Met Cys Ser Asn Leu Leu Glu
1               5                   10

<210> SEQ ID NO 79
<211> LENGTH: 14
<212> TYPE: PRT
```

-continued

```
<213> ORGANISM: Artificial sequence
<220> FEATURE:
<223> OTHER INFORMATION: Synthetic peptide

<400> SEQUENCE: 79

Leu Phe Glu Leu Cys Gly Arg Ala Val Ser Ala His Met Gly
1               5                   10

<210> SEQ ID NO 80
<211> LENGTH: 15
<212> TYPE: PRT
<213> ORGANISM: Artificial sequence
<220> FEATURE:
<223> OTHER INFORMATION: Synthetic peptide

<400> SEQUENCE: 80

Ser Leu Gln His Leu Cys Arg Leu Val Ile Asn Arg Leu Val Ala
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: Synthetic peptide

<400> SEQUENCE: 81

Thr Leu Lys Glu Arg Cys Leu Gln Val Val Arg Ser Leu Val Lys
1               5                   10                  15

<210> SEQ ID NO 82
<211> LENGTH: 24
<212> TYPE: PRT
<213> ORGANISM: Artificial sequence
<220> FEATURE:
<223> OTHER INFORMATION: Synthetic peptide

<400> SEQUENCE: 82

Trp Arg Arg Gln Ala Arg Phe Lys Gly Thr Leu Lys Glu Arg Cys Leu
1               5                   10                  15

Gln Val Val Arg Ser Leu Val Lys
            20
```

CARRIER PEPTIDE FRAGMENT AND USE THEREOF

TECHNICAL FIELD

The present invention relates to a method for transferring (carrying) a foreign substance from outside a eukaryotic cell into the cell, and a carrier peptide fragment used in the method.

The present application claims priority on the basis of Japanese Patent Application No. 2009-177101 filed on 29 Jul. 2009, and the entire content of the domestic application is incorporated into the description of the present application by reference.

BACKGROUND ART

Polypeptides and other foreign substances, particularly biologically active substances, are transferred into the cells of humans and other mammals, etc., (eukaryotic cells) to change the characteristics or to improve and enhance the function of the cells (as well as the tissues and organs comprising the cells).

For example, Patent Document 1 discloses a transcellular carrier peptide for transferring polypeptide, DNA or another foreign substance into a cell. This patent indicates that a polypeptide, DNA, or other biologically active substance can be transferred into a cell with high efficiency by using a carrier peptide conjugate comprising a transcellular carrier peptide linked to a xenogenic polypeptide, DNA, and the like.

Still, a method is needed for changing the characteristics and improving (or enhancing) the function of the cells by easily transferring a full-length polypeptide with a relatively large molecular weight as the foreign substance (biologically active substance) to be transferred into a target cell without the use of special equipment.

Alternatively, in place of transferring a polypeptide or a full-length protein, a method is needed wherein the focus is placed on the specific function of the polypeptide, and a partial amino acid sequence that is the minimum unit capable of expressing that function, i.e., an amino acid sequence (foreign substance) constituting a peptide motif, is transferred efficiently into the cell.

For example, Patent Document 2 discloses part of a peptide chain (amino acid sequence) found in the SOCS protein and other proteins of the same family (hereinafter, "SOCS proteins") that is a motif wherein the amino acid sequence constituting all or part of the specific region called the "BC box," which is believed to bind to the elongin BC complex, has a high level of neuronal differentiation inducing activity on somatic stem cells. Patent Document 2 also discloses that transferring the motif into mammalian somatic stem cells can induce them to differentiate into nerve cells.

PRIOR ART

Patent Document

Patent Document 1: Japanese Patent Publication No. 3854995
Patent Document 2: WO 2007/010989
Patent Document 3: Japanese Patent Application Laid-open No. 2005-330206

Non-Patent Document

Non-Patent Document 1: EMBO Reports, Vol. 10, No. 3, 2009, pages 231 to 238
Non-Patent Document 2: Traffic—International Journal of Intracellular Transport, Vol. 7, 2006, pages 833 to 848
Non-Patent Document 3: PNAS, Vol. 95, 1998, pages 114 to 119
Non-Patent Document 4: Genes & Development, Vol. 12, 1998, pages 3872 to 3881
Non-Patent Document 5: Genes & Development, Vol. 18, 2004, pages 2867 to 2872
Non-Patent Document 6: Genes & Development, Vol. 18, 2004, pages 3055 to 3065

DISCLOSURE OF THE INVENTION

As noted in abovementioned Patent Document 1, however, previous transcellular carrier peptides (e.g., transcellular carrier peptides derived from HIV and *Drosophila*) have a relatively large number of constituent amino acid residues. Thus, there is a need for a peptide (amino acid sequence) for transferring a foreign substance that constitutes a short chain 10 or fewer amino acid residues and that can be synthesized and used efficiently.

Hence, the prevent invention was created in response to this need, and an object of the present invention is to provide a short-chain carrier peptide fragment that has a short amino acid sequence constituting 10 or fewer amino acid residues and is used to transfer a foreign substance from outside a cell (typically a eukaryotic cell, and particularly an animal cell from a mammal, etc., that does not have a cell wall) into the cell. Another object of the present invention is to provide a method that uses this carrier peptide fragment to enable a variety of foreign substances to pass through the cell membrane from outside and transfer the same into a target cell. Moreover, the present invention provides a construct for transferring the foreign substance that has been prepared to comprise the carrier peptide fragment disclosed herein and the foreign substance. Furthermore, the present invention provides a cell, organ, or other biological tissue obtained by transferring the construct comprising the carrier peptide fragment disclosed herein and a foreign substance into the cytoplasm (including into the nucleus) thereof.

The inventors conducted various investigations of peptides (or amino acid sequences constituting parts thereof (i.e., motifs with identified functions)) with previously identified amino acid sequences as peptides having some kind of intracellular function, and they discovered an amino acid sequence that can be preferably used as the abovementioned carrier peptide (fragment) despite having a shorter chain than in the past, thus completing the present invention.

One method provided by the present invention is a process for transferring (carrying) a foreign substance of interest from outside (i.e., outside the cell membrane) of eukaryotic cells (in particular, various animal cells typified by human and other mammalian cells that do not have a cell wall) into the cytoplasm (more preferably, the nucleus) thereof.

More specifically, the method for transferring a foreign substance disclosed herein comprises the steps of:

preparing a construct for transferring a foreign substance that contains a carrier peptide fragment comprising either the amino acid sequence WRRQARFK (SEQ ID NO: 1) or any amino acid sequence formed by the substitution, deletion, and/or addition (insertion) of 1, 2, or 3 amino acid residues in the amino acid sequence, and a foreign substance of interest that is bonded to the N-terminus and/or C-terminus of the carrier peptide fragment;

supplying the abovementioned construct for transferring a foreign substance to a test sample that contains a target eukaryotic cell (typically a culture containing the cell); and incubating the abovementioned test sample that has been supplied with the abovementioned construct for transferring a foreign substance (i.e., maintaining the test sample under conditions enabling survival of the target cell for a predetermined time period) to thereby transfer the construct into the eukaryotic cell in the abovementioned test sample.

The term "foreign substance" used herein refers to an inorganic or organic compound that is capable of bonding either directly or indirectly via a suitable linker to the N-terminus or C-terminus of the abovementioned carrier peptide fragment, and that has a molecular size and chemical properties enabling transfer thereof into a eukaryotic cell.

The inventors discovered that a peptide fragment constituting the partial amino acid sequence "WRRQARFK (SEQ ID NO: 1)" comprising 8 amino acid residues contained in the N-protein (nucleocapsid protein) of IBV (avian infectious bronchitis virus), which belongs to the genus *Coronavirus* and is disclosed in abovementioned Non-Patent Documents 1 and 2, can easily pass through the cell membrane of a target cell, and that the passage through the cell membrane can be realized in the same manner with a construct wherein a foreign substance is bonded to the peptide fragment, thus completing the present invention.

More specifically, the transfer method of the present invention with the abovementioned configuration enables a foreign substance of interest to pass through the cell membrane from outside a eukaryotic cell (outside the cell membrane) and be carried into the cytoplasm (more preferably, pass through the nuclear membrane and into the nucleus) with high efficiency by configuring a construct for transferring a foreign substance by bonding a foreign substance of interest (typically, an organic chemical such as a peptide, nucleic acid, dye, drug, etc.) either directly or indirectly via a suitable linker to the N-terminus and/or C-terminus of the abovementioned carrier peptide (fragment) and supplying that construct to a test sample containing a target eukaryotic cell (typically a culture containing the cell) (in other words, by adding the construct to a living eukaryotic cell).

In one preferred mode of the method for transferring a foreign substance disclosed herein, the abovementioned foreign substance is characterized in that it is any organic compound selected from a group consisting of peptides, nucleic acids, dyes, and drugs.

The term "peptide" used herein refers to an organic compound with a structure wherein two or more amino acids are joined by peptide bonds, and it includes polypeptides (typically, at least 10 but fewer than 300 amino acid residues) and proteins (typically, macromolecular compounds comprising a larger number (300 or more) of amino acid residues than the abovementioned polypeptides).

Moreover, the term "nucleic acid" used herein refers to a nucleotide polymer and includes DNA and RNA.

A construct prepared so that it contains this type of organic compound enables the transfer thereof into the target cell with good efficiency.

Moreover, in another preferred mode of the method for transferring a foreign substance disclosed herein, the abovementioned foreign substance is a peptide, and the abovementioned construct for transferring a foreign substance is a synthetic peptide containing a fragment from a peptide serving as the foreign substance and the abovementioned carrier peptide fragment.

The method of this mode enables a peptide of interest (i.e., the amino acid sequence constituting the peptide) to be transferred into the target cell as a peptide motif in the form of the abovementioned synthetic peptide.

In another preferred mode of the method for transferring a foreign substance disclosed herein, the eukaryotic cell that is the target to which the abovementioned construct for transferring a foreign substance is to be transferred is characterized in that it is a stem cell (including an induced pluripotent stem cell here and hereinafter) derived from a human or other nonhuman mammal.

The present invention enables the transfer of a foreign substance of interest having a designated function into a human or other mammalian stem cell (for example, a somatic stem cell or induced pluripotent stem cell). As a result, the stem cell can be transformed in response to the transferred foreign substance (peptide, etc.), and for example, can differentiate into a specific cell type (nerve cell, bone cell, muscle cell, skin cell, etc.).

Moreover, the present invention provides a construct artificially prepared in order to transfer a foreign substance of interest from outside a eukaryotic cell (in particular, various animal cells typified by human and other mammalian cells that do not have a cell wall) into the cytoplasm (preferably, also into the nucleus) of the cell for realizing the abovementioned object.

In other words, the construct for transferring a foreign substance disclosed herein contains a carrier peptide fragment comprising either the amino acid sequence consisting of WRRQARFK (SEQ ID NO: 1) or any amino acid sequence formed by the substitution, deletion and/or addition (insertion) of 1, 2, or 3 amino acid residues in the amino acid sequence, and a foreign substance of interest that is bonded to the N-terminus and/or C-terminus of the carrier peptide fragment.

A foreign substance of interest can be transferred effectively to a target cell by implementing the transfer method for a foreign substance of the present invention utilizing this construct. In addition, cells to which the foreign substance has been transferred, as well as organs and other body tissues comprising cells that contain the foreign substance can be obtained thereby.

Preferably, as noted above, the abovementioned foreign substance is any organic compound selected from a group consisting of peptides, nucleic acids, dyes, and drugs.

Moreover, most preferably the abovementioned foreign substance is a peptide, and the abovementioned construct for transferring a foreign substance is a synthetic peptide containing a fragment from a peptide serving as the foreign substance and the abovementioned carrier peptide fragment.

BEST MODE FOR CARRYING OUT THE INVENTION

Figure 1:
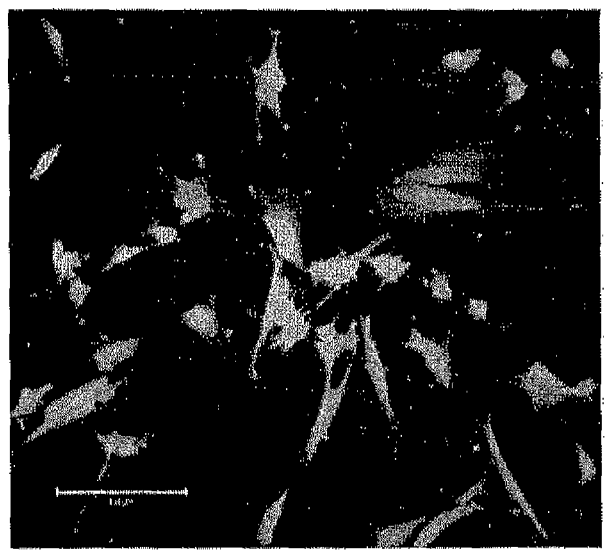
FIG. 1 is a micrograph taken while using a confocal laser scanning microscope to observe a specimen (cells) after human neonate foreskin fibroblasts had been supplied with the construct for transferring a foreign substance (Sample No. 1) as in one example, cultured for 1 hour, and fixed in methanol; the scale in the photo representing 100 μm.

Preferred embodiments of the invention of the present invention are described below. It should also be noted that matters necessary for carrying out the invention beyond those specifically stated in the present description (for example, general matters related to peptide synthesis and cell culture) are understood to be matters of design based on prior art in fields such as medicine, pharmacology, organic chemistry, biochemistry, genetic engineering, protein synthesis, molecular biology, hygiene, and the like.

Moreover, the present invention can be carried out on the basis of the details disclosed herein and common technical knowledge in the fields. It should also be noted that in each instance the amino acids are expressed in the following explanation by single letter codes (by 3-letter codes in the sequence listings) based on the nomenclature for amino acids in the IUPAC-IUB guidelines.

The term "carrier peptide fragment" used herein is a sequence defined (understood) by the amino acid sequence of abovementioned SEQ ID NO: 1, and is an amino acid sequence that exhibits cell membrane permeability (more preferably nuclear localization capability (i.e., nuclear membrane permeability)) in eukaryotic cells.

The specific amino acid sequence represented by SEQ ID NO: 1 herein is a nucleolar localization sequence corresponding to a partial sequence (i.e., motif) comprising a total of 8 amino acid residues that constitute amino acid residues 71 to 78 of the abovementioned nucleocapsid protein (N-protein) of IBV, and the inventors have newly discovered that it exhibits excellent cell membrane permeability. In other words, even though this is a peptide fragment with an extremely short chain consisting of 10 or fewer amino acid residues (in this case, 8 amino acid residues), it can transfer a foreign substance from outside a cell into the cytoplasm.

The “carrier peptide fragment” disclosed herein is typically a sequence identical to the amino acid sequence represented by SEQ ID NO: 1, but in addition thereto, it encompasses an amino acid sequence formed by the substitution, deletion and/or addition (insertion) of one or several (typically 2 or 3) amino acid residues therein without the loss of cell membrane permeability. In other words, such a slightly modified sequence can be easily used by a person skilled in the art on the basis of the information disclosed herein, and therefore is encompassed by the term “carrier peptide fragment” as a technical concept disclosed herein. Typical examples include a sequence produced by so-called conservative amino acid replacement wherein one or several (typically 2 or 3) amino acid residues in the amino acid sequence of SEQ ID NO: 1 are conservatively replaced (for example, a sequence wherein a basic amino acid residue is replaced by a different basic amino acid residue), or a sequence wherein one or several (typically 2 or 3) amino acid residues are added (inserted) to or deleted from the designated amino acid sequence.

The construct for transferring a foreign substance disclosed herein is a construct that can be designed and configured by bonding (linking), either directly or indirectly via a suitable linker, a desired foreign substance to the N-terminus and/or C-terminus of the abovementioned carrier peptide fragment. For example, if the foreign substance is a peptide, the peptide chain can be designed to contain the amino acid sequence constituting the peptide and the amino acid sequence constituting the carrier peptide fragment, and then the intended construct for transferring a foreign substance of interest can be prepared by synthesizing the peptide chain. Moreover, the construct for transferring a foreign substance can be configured by directly or indirectly bonding a nucleic acid such as various types of DNA or RNA, or an organic compound that acts as a dye (for example, a fluorescent compound such as FITC) or that acts as a drug (for example a nucleic acid-based anticancer drug such as 5-fluorouracil (5FU) or an antiviral drug such as azidothymidine (AZT)) to the N-terminus and/or C-terminus of the above carrier peptide fragment by various prior art and publicly known chemical methods.

It should also be noted that when the foreign substance is a peptide, the peptide (amino acid sequence) to be used is not particularly limited herein. A polypeptide or protein with a relatively large number of amino acid residues, for example about 100 to 1000 amino acid residues, can be used as the foreign substance.

Typically, a suitable number for the total number of amino acid residues constituting the synthetic peptide prepared as the construct for transferring a foreign substance is 1000 or fewer, preferably 600 or fewer, and even more preferably 500 or fewer, and most preferably 300 or fewer (and further, 100 or fewer, e.g., 10 to 50). Such a relatively short peptide is easy to synthesize and easy to use.

Preferably, the foreign substance to be used is a mature form or precursor (including pro-forms and prepro-forms) of a peptide (including polypeptides and proteins) involved in a function such as the development, differentiation, growth, malignant transformation, homeostasis, and regulation of metabolism in various cells and tissues (organs). Moreover, the present invention can be carried out to transfer a peptide with a heretofore unknown function into a cell to elucidate the function of the peptide with the cell (within a biological tissue).

For example, when the eukaryotic cell that is the target of transfer is a human or other mammalian stem cell (including somatic stem cells, embryonic stem cells, and induced pluripotent stem cells (hereinafter, iPS cells)), preferably the mature form or precursor of a peptide with various types of biological activity involving the induction of differentiation of the stem cell will be used. Moreover, when the eukaryotic cell that is the target of transfer is a cancer cell (tumor cell), preferably various peptides involved in the induction of apoptosis of the cancer cell (tumor cell) will be used.

Alternatively, in the past iPS cells have been prepared by transducing a plurality of genes (for example, Oct3/4, Sox2, Klf4, c-Myc, Nanog, Lin28) into a designated cell (for example, a human or other mammalian skin cell or other somatic cell), and at least one gene product (peptide) from among these genes can be transferred by the transfer method of the present invention in place of the technique. Thus, it will be possible to prepare iPS cells by transferring the products of the abovementioned genes (i.e., peptides) into the cells (preferably the nucleus) in place of the direct transduction of the genes.

Therefore, an example of one preferred embodiment of the present invention is a method for preparing iPS cells wherein the construct for transferring a foreign substance of the present invention is prepared using as the foreign substance a peptide (for example Sox2 protein), encoded by at least one of a plurality of genes (for example Sox2) involved in the preparation of iPS cells, and the construct is then transferred into a designated eucaryotic cell (such as a human dermal fibroblast, etc.)

Moreover, a variety of previously known sequence motifs (peptide motifs) can be used therefor. For example, when the eukaryotic cell that is the target of transfer is a human or other mammalian stem cell (including somatic stem cells, embryonic stem cells, and iPS cells), preferably a variety of peptide motifs involved in inducing differentiation of the stem cell will be used. Moreover, when the eukaryotic cell that is the target of transfer is a cancer cell (tumor cell), preferably various peptide motifs involved in inducing apoptosis of the cancer cell (tumor cell) will be used.

Prime examples of peptide motifs that can be used most preferably in the examples of the present application include the various amino acid sequences (motifs) disclosed in Patent Document 2 above that exhibit neurodifferentiation properties.

In other words, Patent Document 2 discloses partial amino acid sequences constituting the various SOCS (suppressor of cytokine signaling) proteins and other proteins of the same family (hereinafter, "SOCS proteins") that all have a SOCS-box, which is a region (amino acid sequence) that can bind to the elongin BC complex (specifically, a part of elongin C), which is known to form a complex with elongin A and act as a transcription regulating factor. Patent Document 2 also indicates that this amino acid sequence, which is contained in a specific region called the "BC-box" that is believed to bind with the elongin BC complex, has a high level of neurodifferentiation inducing activity in somatic stem cells.

SEQ ID NOS: 2 to 19 are typical examples of amino acid sequences that are contained in the BC-box of various proteins identified as SOCS proteins (see Non-Patent Documents 3 to 6).

More specifically, these represent amino acid sequences comprising 15 contiguous amino acid residues from the N-terminus of the BC-boxes contained in mSOCS-1 (SEQ ID NO: 2), mSOCS-2 (SEQ ID NO: 3), mSOCS-3 (SEQ ID NO: 4), mSOCS-4 (SEQ ID NO: 5), mSOCS-5 (SEQ ID NO: 6), hSOCS-6 (SEQ ID NO: 7), hSOCS-7 (SEQ ID NO: 8), hRAR-1 (SEQ ID NO: 9), hRAR-like (SEQ ID NO: 10), mWSB-1 (SEQ ID NO: 11), mWSB-2 (SEQ ID NO: 12), mASB-1 (SEQ ID NO: 13), mASB-2 (SEQ ID NO: 14), hASB-3 (SEQ ID NO: 15), LRR-1 (SEQ ID NO: 16), hASB-7 (SEQ ID NO: 17), mASB-10 (SEQ ID NO: 18) and hASB-14 (SEQ ID NO: 19) (see Non-Patent Documents 3 to 6).

Moreover, although a specifically detailed explanation is omitted herein, SEQ ID NOS: 20 to 80 represent amino acid sequences contained in the BC-boxes of various SOCS proteins identified in viruses (HIV, AdV, SIV, etc.) and in mammals, and the peptides comprising the sequences. For example, SEQ ID NOS: 75 and 79 are amino acid sequences contained in the BC-box of a SOCS protein (MUF1) identified from humans. Moreover, SEQ ID NO: 80 is the amino acid sequence contained in the BC-box of a SOCS protein mCIS (cytokine-inducible $SH_2$-containing protein) identified from mice.

These are merely examples, and there is no intention herein to limit the amino acid sequences (motifs) constituting the BC-box to these sequences. When the present application was filed amino acid sequences constituting various BC-boxes had been disclosed in a number of published documents and there is no need for further listing of examples herein. These amino acid sequences can be easily found through conventional search methods.

In one preferred embodiment of the present invention, the synthetic peptide to be transferred to a target eukaryotic cell (for example, a somatic stem cell from a human or nonhuman mammal) can be configured using any of the above amino acid sequences originating in the BC-box (typically any amino acid sequence from SEQ ID NOS: 2 to 80) as a peptide motif (sequence motif) that is involved in inducing neurodifferentiation. Therefore, in accordance with the abovementioned explanation, the present invention provides a method for inducing the differentiation of at least one type of eukaryotic cell into a nerve cell. In other words, this method includes the steps of first synthesizing a peptide chain featuring an amino acid sequence originating in any BC-box (typically a sequence comprising at least 10 contiguous amino acid residues (for example at least 10 residues starting from the N-terminus) selected from any amino acid sequence represented by SEQ ID NOS: 2 to 80) as a peptide motif involved in inducing neurodifferentiation bonded to the N-terminal end or C-terminal end of the abovementioned carrier peptide fragment according to the present invention, and then supplying the synthetic peptide (i.e., an artificial peptide that is the construct for transferring a foreign substance) to a test sample containing a target eukaryotic cell or tissue comprising the cell (typically a culture product containing the cell). Typically, this also includes incubation of the test sample to which the synthetic peptide is supplied.

Moreover, it is clear from the abovementioned explanation that the present invention provides an artificial peptide used in a method for inducing such differentiation to a nerve cell and a method for preparing the same.

In other words, the artificial peptide of this configuration (neurodifferentiation-inducing peptide) can be synthesized so that it provides an amino acid sequence originating in any BC-box (hereinafter called a "BC-box-related sequence" and typically a sequence comprising at least 10 contiguous amino acid residues (for example at least 10 residues starting from the N-terminus) selected from any amino acid sequence represented by SEQ ID NOS: 2 to 80) as a peptide motif involved in inducing neurodifferentiation bonded onto the N-terminal end or C-terminal end of the abovementioned carrier peptide fragment.

Alternatively, the amino acid sequence of 15 contiguous amino acid residues represented by SEQ ID NO: 81 can be used for the same purpose as the abovementioned BC-box-related sequence. In other words, as disclosed in Patent Document 3, the amino acid sequence represented by SEQ ID NO: 81 is a partial amino acid sequence comprising 15 contiguous amino acid residues from residues 157 to 171 of the amino acid sequence of the Von Hippel-Lindau (VHL) protein, which is known to exhibit neurodifferentiation-inducing capability (i.e., SEQ ID NO: 81 is a VHL-related peptide motif).

Furthermore, just as in the case of the carrier peptide fragment of the present invention disclosed above, it is surely possible to use a modified amino acid sequence or peptide motif (foreign substance) involved in inducing neurodifferentiation that is formed by the replacement, deletion, and/or addition (insertion) of 1 or several (for example, 5 or less, and typically 2 or 3) amino acid residues therein provided its function as a peptide motif related to inducing neurodifferentiation is retained.

The construct for transferring a foreign substance with the abovementioned configuration has a high level of neurodifferentiation-inducing activity toward at least one type of cell (typically a stem cell) as a neurodifferentiation-inducing peptide. Hence, it can most suitably be used as an active ingredient in a neurodifferentiation-inducing agent. It should be noted that the neurodifferentiation-inducing peptide contained in the neurodifferentiation-inducing agent can also take the form of a salt provided the neurodifferentiation-inducing activity thereof is not lost. For example, an acid addition salt of the peptide that is obtained by carrying out an addition reaction with a conventionally used inorganic or organic acid by conventional means can be used therefor. Alternatively, a different salt (for example, a metal salt) can be used provided it has neurodifferentiation-inducing activity.

The neurodifferentiation-inducing agent can contain a neurodifferentiation-inducing peptide of the abovementioned constitution as the active ingredient, as well as various medically (pharmaceutically) permissible carriers in accordance with the form of use. A carrier generally used in peptide medicines is preferably used as a diluent, excipient, and the like. The carrier will differ appropriately in accordance with the usage and form of the neurodifferentiation-inducing agent, but typical examples include water, a physiological buffer solution, and various organic solvents. The carrier can be an aqueous solution of alcohol (ethanol, etc.) at a suitable concentration, glycerol, or a non-drying oil such as olive oil. Alternatively, the carrier can be a liposome. Examples of a secondary ingredients that can be contained in the neurodifferentiation-inducing agent include various fillers, expanders, binders, moisturizers, surfactants, pigments, fragrances, etc.

The form of the neurodifferentiation-inducing agent is not particularly limited herein. Examples of typical forms include liquids, suspensions, emulsions, aerosols, foams, granules, powders, tablets, capsules, and ointments. Moreover, the agent can also be made into a lyophilized product or granulated product to be dissolved in physiological saline or a suitable buffer (e.g., PBS), etc., immediately before use and prepared as a liquid for injection, etc.

It should also be noted that prior art, publicly known methods can be used for the processes themselves whereby the neurodifferentiation-inducing peptide (main ingredient) and various carriers (secondary ingredients) are made into a material and then prepared as the medicines (compositions) in various forms, and a detailed explanation of the production process for drug product formulation itself is omitted herein because it is not a characterizing feature of the present invention. For example, *Comprehensive Medicinal Chemistry*, edited by Corwin Hansch, Pergamon Press, 1990, can be noted as a source of detailed information concerning formulations.

The dosage and administration of the neurodifferentiation-inducing agent provided by the present invention can be suited to the form and purpose thereof.

For example, exactly the desired amount of the neurodifferentiation-inducing peptide synthesized to contain a BC-box-related sequence or VHL peptide motif and the carrier peptide fragment disclosed herein (in other words, the neurodifferentiation-inducing agent comprising the synthetic peptide) can be administered as a liquid medicine to a patient (i.e., to the body) by intravenous, intramuscular, subdermal, intradermal, or intraperitoneal injection. Alternatively, it can be administered orally in solid form such as a tablet, etc. Thus, typically neurons can be generated (produced) in vivo from somatic stem cells present at or near the diseased area. As a result, nerve regeneration can serve as a powerful therapeutic method that can effectively treat a variety of neurological disorders. For example, treatment of neurological disorders such as Parkinson's disease, cerebral infarction, Alzheimer's disease, paralysis of the body caused by trauma to the spinal cord, cerebral contusion, amyotrophic lateral sclerosis, Huntington's disease, brain tumor, retinal degeneration, and the like can be treated with a regenerative medicine approach.

Alternatively, by supplying a suitable amount of neurodifferentiation-inducing agent (neurodifferentiation-inducing peptide) to cellular material that has been temporarily or permanently resected from the body, i.e., living tissue or cell clusters (for example, a culture product of somatic stem cells), a target peptide motif (BC-box-related sequence, etc.) can be transferred efficiently from outside the cells into the cytoplasm (more preferably, the nucleus) thereof, and neurons can be efficiently generated thereby. This means that large amounts of the desired neurons can be produced in the cellular material. Furthermore, by returning the neurons that were produced in large amounts or cellular material (living tissues and cell clusters) containing the produced neurons once again to the body (typically a diseased area requiring nerve regeneration), the same therapeutic efficacy can be obtained as when the neurodifferentiation-inducing agent (neurodifferentiation-inducing peptide) is administered directly to the body.

It is clear from the above explanation that, in a different aspect, the present invention can provide cells, cell clusters, and living tissues that are useful for treating neurological disorders and wherein differentiation to neurons has been induced by using any of the neurodifferentiation-inducing peptides of the abovementioned configurations disclosed herein.

Moreover, a polynucleotide coding for the neurodifferentiation-inducing peptide of the present invention can be used as a material for so-called gene therapy. For example, the neurodifferentiation-inducing peptide of the present invention can be expressed constantly in the body (cells) by incorporating a gene (typically a DNA segment or RNA segment) coding for the neurodifferentiation-inducing peptide into a suitable vector, and transfecting a target site therewith. Therefore, a polynucleotide (DNA segment, RNA segment, etc.) coding for the neurodifferentiation-inducing peptide of the present invention is useful as a drug for the prevention or treatment of a neurological disease in the abovementioned patients, etc.

At least one amino acid residue can be amidated in the construct for transferring a foreign substance (i.e., an artificially synthesized peptide) wherein the foreign substance is a peptide provided by the present invention such as the abovementioned neurodifferentiation-inducing peptide that is presented as a typical example. The structural stability (protease resistance) of the peptide in the cytoplasm and nucleus can be increased by amidation of the carboxyl group of an amino acid residue (typically the C-terminal amino acid residue of a peptide chain).

It is desirable for the total number of amino acid residues in the peptide chain constituting the artificial peptide to be 1000 or fewer (preferably, 600 or fewer, and particularly preferably 300 or fewer, e.g., 50 or fewer). Such a short peptide can be easily configured by chemical synthesis methods, and therefore can be easily supplied to a test sample containing the target eukaryotic cells.

It should also be noted that the conformation (three-dimensional structure) of the peptide is not particularly limited, but preferably it is a straight chain or helix from the standpoint of its not easily becoming an immunogen (antigen).

It should also be noted that as an artificial peptide preferably all of the amino acid residues are L-amino acids, but provided the desired function inherent in the carrier peptide fragment and peptide motif is not lost, part or all of the amino acid residues can be replaced by D-amino acids.

Moreover, an additional sequence that normally cannot occur in these sequences can be partly included therein provided the desired function inherent in the carrier peptide fragment and peptide motif is not lost. For example, an amino acid sequence can be configured with a structure wherein several amino acid residues functioning as a linker (for example, glycine residues) can be positioned between the carrier peptide fragment and the foreign peptide motif.

Among artificial peptides (constructs for transferring a foreign substance) to be used, those with a relatively short peptide chain can easily be produced by conventional chemical synthesis methods. For example, a either prior art publicly known solid phase or liquid phase synthesis method can be used. Solid phase synthesis using Boc (t-butyloxycarbonyl) or Fmoc (9-fluoroenylmethoxycarbonyl) as an amine protecting group is preferred. In other words, a peptide chain with the desired amino acid sequence and modifications (C-terminal amidation, etc.) can be synthesized by solid phase synthesis using a commercially available peptide synthesizer (e.g., one obtainable from PerSeptive Biosystems, Applied Biosystems, etc.)

Alternatively, the artificial peptide (construct for transferring a foreign substance) can be synthesized using genetic engineering methods. This approach is preferred for producing a polypeptide with a relatively long peptide chain. In other words, a DNA nucleotide sequence (including the ATG start codon) that codes for the amino acid sequence of the desired artificial peptide is synthesized. Then a recombinant vector suitable for a host cell is configured with a genetic construct for expression that comprises the DNA and various regulatory elements (including a promoter, ribosome binding site, terminator, enhancer, and a cis-element for controlling the level of expression) to express the amino acid sequence in the host cell.

Using conventional techniques this recombinant vector is transferred to designated host cells (for example, yeast cells, insect cells, plant cells, or animal (mammal) cells), and the host cells, or an individual or tissue containing the cells is cultured under designated conditions. The target polypeptide can be expressed and produced in the cells thereby. Furthermore, a peptide comprising the target amino acid sequence can be obtained by isolating and purifying the polypeptide from the host cells (or from the culture medium if it is secreted). Using conventional techniques this recombinant vector is transferred to a designated host cell (for example, yeast, insect cell, plant cell, or mammalian cell), and the host cell, or an individual or tissue containing the cells is cultured under prescribed conditions. The target polypeptide can be expressed and produced in the cells thereby. Then the target peptide (i.e., construct for transferring a foreign substance) can be obtained by isolating and purifying the polypeptide from the host cells (or from the culture medium if it is secreted).

It should be noted that the method for configuring the recombinant vector and the method for transferring the configured recombinant vector to a host cell, etc., can utilize methods conventionally used in the fields without modification, and because those methods themselves are not a characterizing feature of the present invention, the detailed explanation thereof is omitted herein.

For example, a fusion protein expression system can be used for efficient, large volume production in host cells. More specifically, first the gene (DNA) coding for the amino acid sequence of the target peptide is prepared by chemical synthesis, and the synthesized gene is inserted at a suitable site in a suitable fusion protein expression vector (for example, a GST (glutathione S-transferase) fusion protein expression vector such as the pET series provided by Novagen and the pGEX series provided by Amersham Biosciences). Then the host cells (typically E. coli) are transformed by the vector. The resulting transformant is cultured to prepare the target fusion protein. Next the protein is extracted and purified. Then the resulting purified is cleaved by a designated enzyme (protease) and the freed target peptide fragment (i.e., the designed artificial peptide) is recovered by a method such as affinity chromatography. The target construct for transferring a foreign substance (artificial peptide) can be produced using this kind of prior art and publicly known fusion protein expression system (for example, the GST/His system provided by Amersham Biosciences can be utilized).

Alternatively, template DNA for use in a cell-free protein synthesis system (i.e., a synthetic gene fragment containing a nucleotide sequence coding for the amino acid sequence of the target artificial peptide) can be prepared, and in vitro synthesis of the target polypeptide can be carried out by employing a so-called cell-free protein synthesis system using the various compounds necessary for peptide synthesis (ATP, RNA polymerase, amino acids, etc.). References concerning a cell-free protein synthesis system include the papers by Shimizu et al. (Shimizu et al., Nature Biotechnology, 19, 751-755 (2001)), and Madin et al. (Madin et al., Proc. Natl. Acad. Sci. USA, 97(2), 559-564 (2000)). When the present application was filed there were already many companies carrying out polypeptide production on consignment based on the technology disclosed in these documents, and cell-free protein synthesis kits were commercially available (for example the wheat germ cell-free protein synthesis kit PROTEIOS® obtainable from Toyobo Co., Ltd., in Japan).

Therefore, if an amino acid sequence (for example, the BC-box-related sequence noted above) corresponding to the peptide motif that is the object of transfer into the cytoplasm (preferably, the nucleus) can be determined, and a peptide chain can be designed that combines the same with the cell membrane-permeating carrier peptide fragment represented by abovementioned SEQ ID NO: 1, the intended artificial peptide can easily be synthesized and produced by a cell-free protein synthesis system based on its amino acid sequence. For example, the peptide can easily be produced with the PURESYSTEM® from Japan's Post Genome Institute Co., Ltd.

Several examples concerning the present invention are described below, but the present invention is by no means limited to the items presented in these examples.

EXAMPLE 1

Preparation of Construct for Transferring a Foreign Substance

A total of two types of peptides (Sample No. 1 and Sample No. 2) described below were produced using a peptide synthesizer. Table 1 shows the amino acid sequences of these synthetic peptides.

TABLE 1

| Peptide No. | Structure (amino acid sequence) | | Total amino acid residues |
|---|---|---|---|
| Peptide 1 | WRRQARFK | (SEQ ID NO: 1) | 8 |
| Peptide 2 | WRRQARFK-G-TLKERCLQVVRSLVK | (SEQ ID NO: 82) | 24 |

As shown in Table 1, Peptide 1 comprises the carrier peptide fragment of SEQ ID NO: 1 in the present invention.

Moreover, Peptide 2 is configured to have the abovementioned VHL peptide motif (SEQ ID NO: 81) as a peptide fragment to serve as the foreign substance on the C-terminal end interposed by a single glycine residue on the C-terminal end linker of the carrier peptide fragment represented by SEQ ID NO: 1. (It should be noted that the hyphen in the amino acid sequence shown in Table 1 was added for easy understanding of the structure of the amino acid sequence.) It should also be noted that in each peptide the carboxyl group (—COOH) of the C-terminal amino acid is amidated (—$CONH_2$). Both peptides were synthesized using solid phase synthesis (Fmoc method) using a commercially available peptide synthesizer (Intavis AG) and following the instruction manual. It should also be noted that a detailed explanation of the mode of use of the peptide synthesizer itself has been omitted herein because it is not a characterizing feature of the present invention.

The two constructs for transferring a foreign substance of the present examples were prepared by bonding a fluorescent dye as a foreign substance to the N-terminal end of abovementioned Peptide 1 and Peptide 2.

More specifically, as a fluorescent dye commonly used FAM (i.e., $C_{21}H_{12}O_7$: 5(6)-carboxyfluorescein, molecular weight 376.3) was bonded directly to the N-terminus of abovementioned Peptide 1 in a conventional method to prepare "(FAM)-WRRQARFK," a construct for transferring a foreign substance based on Peptide 1. This is called Sample No. 1 below.

Alternatively, as a fluorescent dye commonly used FITC (i.e., $C_{21}H_{11}NO_5S$: fluorescein isothiocyanate, molecular weight 389.4) was bonded indirectly via the well-known linker Acp, in other words, 6-aminohexanoic acid (6-aminocaprioic acid, molecular weight 131.2) to the N-terminus of abovementioned Peptide 2 in a conventional method to prepare "(FITC)-(Acp)-WRRQARFKGTLKERCLQV-VRSLVK," a construct for transferring a foreign substance based on Peptide 2. This is called Sample No. 2 below.

The sample peptides prepared in this way were each diluted in PBS (phosphate buffered saline) to prepare a total of two types of sample solutions with a sample (peptide) concentration of 1 mM.

EXAMPLE 2

Evaluation of Cell Membrane Permeability Function of Sample No. 1 and Sample No. 2 (1)

Human neonate foreskin fibroblasts (ATCC Catalogue No. CRL-2097) were used as the eukaryotic cells, and the cell membrane permeability capability of the two samples (constructs for transferring a foreign substance) obtained in Example 1 above was investigated.

More specifically, the abovementioned fibroblasts were cultured in a liquid mixture of 90% Eagle MEM culture medium (containing 0.1% nonessential amino acids, 2 mM L-glutamine, 1 mM sodium pyruvate, and 1.5 g/L sodium hydrogen carbonate) and 10% serum (FBS) as the culture medium.

The cultured cells were trypsinized for 1 min at 37° C. with a 0.25% trypsin solution. After the abovementioned treatment, the trypsin was deactivated with FBS-containing medium, and a cell suspension (test sample for foreign substance transfer) was prepared by adjusting the cell concentration to approximately $5 \times 10^4$ cells/mL with the culture medium.

Next, 0.5 mL of the abovementioned cell suspension was placed in a designated cell culturing container (culture slide with a surface coating of 0.1% gelatin), and the cells were incubated overnight at 37° C. in a 5% $CO_2$ atmosphere. After incubation the medium was replaced with fresh culture medium, and the 1 mM sample solutions of each of the samples prepared in abovementioned Example 1 were added to a cell culture container so that the final sample concentration (peptide concentration) would be 1 μM. In this case 0.5 μL of sample solution was added to the container. Then the samples were incubated at 37° C. for either 1 or 4 hours in a 5% $CO_2$ atmosphere.

The cells after 1 hour of culture and the cells after 4 hours of culture were each rinsed in PBS (phosphate buffered saline) and fixed with methanol (on ice for 10 min).

Next the methanol-fixed samples (cells) were mounted using Prolong® Gold Antifade Reagent (Invitrogen) that contains the nuclear stain DAPI (4',6-diamidino-2-phenylindole). Then the localization within the cells of the peptide bonded to the fluorescent dye (i.e., fluorescently labeled peptide) in each test sample (i.e., the abovementioned mounted test samples after methanol fixation) was verified using a confocal scanning laser microscope.

Figure 2:
FIG. 2 is a micrograph taken while using a confocal laser scanning microscope to observe a specimen (cells) after human neonate foreskin fibroblasts had been supplied with the construct for transferring a foreign substance (Sample No. 1) as in one example, cultured for 4 hours, and fixed in methanol; the scale in the photo representing 100 μm.

FIGS. 1 and 2 are micrographs showing the results when abovementioned Sample No. 1 was added to the liquid suspension of cells. FIG. 1 shows the results in the test sample after 1 hour of culture, and FIG. 2 shows the same after 4 hours of culture.

As the micrographs clearly show, it was confirmed that abovementioned added Sample No. 1 penetrated the cell membrane from outside the cell rapidly after it was added, and thus was transferred into the cells. In addition, from the results of the nuclear staining by DAPI it was confirmed that some of Sample No. 1 that had been transferred into the cytoplasm had translocated into the nucleus (i.e., had been transferred into the nucleus). Although the micrographs are not shown here, similar results were obtained with Sample No. 2.

In other words, it was confirmed that a total of two types of constructs for transferring a foreign substance (Sample No. 1 and Sample No. 2) that were obtained in Example 1 above exhibited excellent cell membrane permeability resulting from inclusion of the abovementioned carrier peptide fragment.

EXAMPLE 3

Evaluation of Cell Membrane Permeability Function of Sample No. 1 and Sample No. 2 (2)

The target cells for transferring the foreign substance were changed from human neonate foreskin fibroblasts to human iPS cells (human induced pluripotent stem cells), and the cell membrane permeability capability of the two samples (constructs for transferring a foreign substance) obtained in Example 1 above was investigated. It should also be noted that the iPS cells (cell line 201B2-082008KU) and the mouse embryonic fibroblast feeder cells (cell line SNL 76/7, hereinafter "MEF") used in this example were provided by the Yamanaka Research Laboratory of the Institute for Frontier Medical Sciences, Kyoto University (professor Shinya Yamanaka).

First the obtained MEF were inactivated by a mitomycin C treatment (3 hours) and then trypsinized in a 0.25% trypsin solution containing 1 mM EDTA. After the above treatment, the trypsin was deactivated with culture medium containing FBS, and the MEF were adjusted to a suitable cell density using D-MEM medium (Dulbecco's Modified Eagle Medium: Gibco) containing MEF culture medium (7% FBS:

Gibco), 2 mM L-glutamine (Gibco), 50 units/mL penicillin, and 50 µg/mL streptomycin (Gibco), and the abovementioned MEF were seeded onto a culture container (in the form of a culture slide or plate) with a surface coating of 0.1% gelatin. In this case, the MEF were seeded so that the cell density would be approximately $1.25 \times 10^5$ cells/mL. Next, the abovementioned cell culture containers were incubated overnight at 37° C. in a 5% $CO_2$ atmosphere.

Thereafter, the feeder cells were prepared by removing the MEF culture medium and rinsing with PBS.

Separately, CTK solution (0.25% trypsin solution containing 0.1 mg/mL collagenase IV (Gibco), 1 mM calcium chloride, and 20% KSR (KnockOut® Serum Replacement)) was added to the obtained iPS cell line, the MEF were peeled therefrom, and the cells were rinsed with PBS.

Next, 1 mL hESC culture medium (i.e., human ES cell medium, in this case, DMEM/F12 culture medium (Gibco) containing 20% KSR (Gibco), 2 mM L-glutamine (Gibco), 0.1% nonessential amino acids (Gibco), 0.1 mM 2-mercaptoethanol (Gibco), 50 units/mL penicillin, and 50 µg/mL streptomycin (Invitrogen, 4 ng/mL bFGF (basic fibroblast growth factor)) was added, the iPS cells were peeled off using a cell scraper, and the colony was broken apart by gentle pipetting.

A suspension of iPS cells obtained in this manner was seeded onto the feeder cells in the culture containers that had been prepared as described above. Then, the abovementioned hESC medium was added, and the cell culture containers were incubated overnight at 37° C. in a 5% $CO_2$ atmosphere.

After incubation overnight, the culture medium was removed from the culture containers, and the abovementioned hESC medium to which one of the 1 mM sample solutions prepared in abovementioned Example 1 had been added to make a final sample concentration (pipetted concentration) of 1 µM was added to the culture containers. Then the samples were incubated at 37° C. for either 1 or 4 hours in a 5% $CO_2$ atmosphere.

The cells after 1 hour of culture and cells after 4 hours of culture were each rinsed in PBS (phosphate buffered saline) and fixed with methanol (on ice for 10 min).

Figure 3:
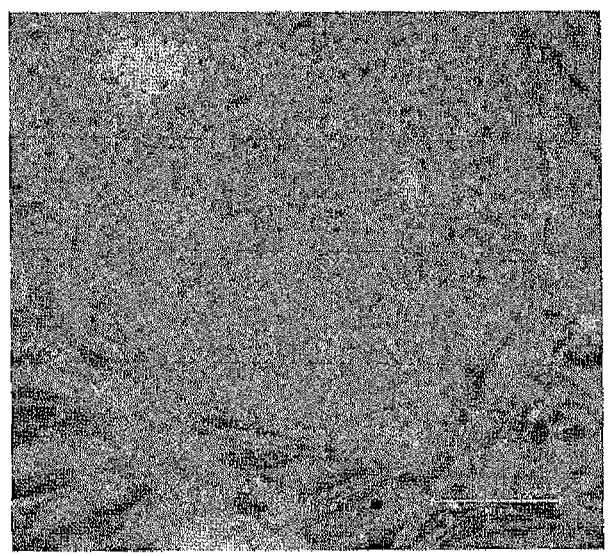
FIG. 3 is a micrograph taken while using a confocal laser scanning microscope to observe a specimen (cells) after iPS cells had been supplied with the construct for transferring a foreign substance (Sample No. 1) as in one example, cultured for 1 hour, and fixed in methanol; the scale in the photo representing 100 μm.
Figure 4:
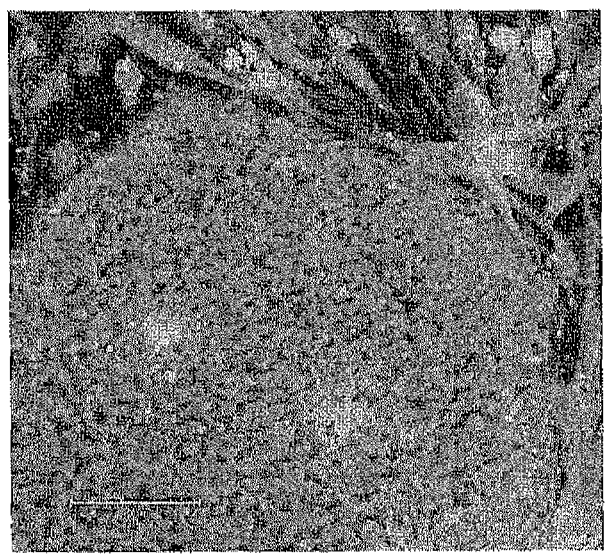
FIG. 4 is a micrograph taken while using a confocal laser scanning microscope to observe a specimen (cells) after iPS cells had been supplied with the construct for transferring a foreign substance (Sample No. 2) as in one example, cultured for 1 hour, and fixed in methanol; the scale in the photo representing 100 μm.

Next, the same treatment as in Example 2 was performed, and the localization within the iPS cells of the peptide that was bonded to the fluorescent dye (i.e., fluorescently labeled) was verified using a confocal scanning laser microscope. FIG. 3 is a micrograph showing the results after 1 hour of culture of the cell suspension to which abovementioned Sample No. 1 had been added, and FIG. 4 is a micrograph after 1 hour of culture of the cell suspension to which abovementioned Sample No. 2 had been added.

As the micrographs clearly show, it was confirmed that the abovementioned added Sample Nos. 1 and 2 both penetrated the cell membrane from outside the cell rapidly after addition and were transferred into the cells. In addition, from the results of the nuclear staining with DAPI it was confirmed that some of Sample Nos. 1 and 2, which had been transferred into the cytoplasm, had further translocated into the nucleus (i.e., had been transferred into the nucleus). In other words, it was confirmed that a total of two types of constructs for transferring a foreign substance (Sample No. 1 and Sample No. 2) that were obtained in Example 1 above exhibited excellent cell membrane permeability resulting from inclusion of the abovementioned carrier peptide fragment, and it was found that not only a fluorescent dye, but a peptide serving as a foreign substance (in this case, the VHL peptide represented by SEQ ID NO: 81) can efficiently pass through the cell membrane from outside the cell and can be transferred (carried) into the cytoplasm, and even into the nucleus.

These findings clearly show that as a particularly preferred mode of the method for transferring a foreign substance disclosed herein, the present invention provides a method for transferring a foreign substance of interest from outside a human or nonhuman mammalian stem cell (particularly, an ES cell, iPS cell or somatic stem cell) into the cytoplasm of the cell (more preferably into the nucleus as well) by using a carrier peptide fragment comprising the amino acid sequence of SEQ ID NO: 1 or a modified amino acid sequence thereof formed by the substitution, deletion and/or addition (insertion) of 1, 2, or 3 amino acid residues in the amino acid sequence as the abovementioned carrier peptide fragment. The carrier peptide fragment comprising the amino acid sequence of abovementioned SEQ ID NO: 1 is preferred for transferring a protein (typically about 300 to 1000 (for example, about 300 to 600) amino acid residues), a polypeptide of fewer than 300 amino acid residues, or a peptide motif with 100 or fewer (especially 50 or fewer) amino acid residues into a stem cell, particularly an iPS cell, ES cell, and the like.

Specific examples of the present invention have been described in detail above, but these are merely exemplary and by no means limit the scope of the claims herein. The technology disclosed in the claims includes various changes to and variations of the specific examples presented above.

INDUSTRIAL APPLICABILITY

The present invention enables the transfer of a foreign substance of interest having a designated function into a human or other mammalian stem cell (for example, a somatic stem cell and induced pluripotent stem cell) or other target cell. Thereby it is possible to transform the target cell in accordance with the foreign substance (peptide, etc.) to be transferred, and for example, bring about the differentiation thereof to a specific cell type (nerve cell, bone cell, muscle cell, skin cell, etc.)

The present invention provides an artificially prepared construct for transferring a foreign substance of interest from outside a eukaryotic cell (in particular, various animal cells typified by human and nonhuman mammalian cells that do not have a cell wall) into the cytoplasm (preferably, the nucleus as well) thereof. By utilizing this construct a foreign substance of interest can be effectively transferred into a target cell, and cells wherein the foreign substance has been transferred, as well as organs and other body tissues comprising cells that contain the foreign substance can be obtained thereby.

Sequence Listing Free Test

Synthetic Peptides of SEQ ID NOS: 1 to 82

The invention claimed is:

1. A method for transferring a foreign substance of interest from outside a human or other mammalian cell into the cytoplasm of the cell, comprising the steps of:
   preparing a construct containing:
   a carrier peptide fragment consisting of the amino acid sequence set forth in SEQ ID NO: 1; and
   a foreign substance of interest that is bonded directly or indirectly via a linker to the N-terminus and/or C-terminus of the carrier peptide fragment;
   adding the construct containing the carrier peptide fragment to a culture medium that includes the human or other mammalian cell or a tissue containing the cell;
   culturing the human or other mammalian cell or the tissue containing the cell in the medium containing the construct; and
   transferring the construct into the culturing human or other mammalian cell from outside of the cell by cell membrane permeability of the carrier peptide fragment itself.

2. The method according to claim 1, wherein the foreign substance is any organic compound selected from the group consisting of peptides, nucleic acids, dyes, and drugs.

3. The method according to claim 2, wherein the foreign substance is a peptide, and the construct for transferring a foreign substance is a synthetic peptide containing a fragment from a peptide serving as the foreign substance, and the carrier peptide fragment.

4. The method according to claim 1, wherein the human or other mammalian cell is a stem cell originating in a human or other mammal.

\* \* \* \* \*